US007988958B2

(12) United States Patent
Stern et al.

(10) Patent No.: US 7,988,958 B2
(45) Date of Patent: Aug. 2, 2011

(54) ENTEROCOCCUS AND STREPTOCOCCUS STRAINS AND BACTERIOCINS (75) Inventors: Norman J. Stern, Athens, GA (US); John E. Line, Watkinsville, GA (US); Edward A. Svetoch, Moscow Region (RU); Boris V. Eruslanov, Moscow Region (RU); Vladimir V. Perelygin, Moscow Region (RU); Eugeni V. Mitsevich, Moscow Region (RU); Irina P. Mitsevich, Moscow Region (RU); Vladimir P. Levchuk, Moscow Region (RU)

(73) Assignees: The United States of America as represented by the Secretary of Agriculture, Washington, DC (US); State Research Center for Applied Microbiology & Biotechnology, Ministry of Health & Social Development, RF, as represented by the Director of the State Research Center for Applied Microbiology & Biotechnology Ministry of Health & Social Development, RF, Obolensk (RU)

( * ) Notice: Subject to any disclaimer, the term of this patent is extended or adjusted under 35 U.S.C. 154(b) by 1373 days.

(21) Appl. No.: 11/099,456

(22) Filed: Apr. 5, 2005

(65) Prior Publication Data
US 2006/0223161 A1    Oct. 5, 2006

(51) Int. Cl.
*A01N 63/00*    (2006.01)
*A61K 39/02*    (2006.01)
*A01K 45/00*    (2006.01)

(52) U.S. Cl. ................... 424/93.1; 424/93.4; 424/190.1; 424/282.1

(58) Field of Classification Search ................. 435/71.3, 435/253.4
See application file for complete search history.

(56) References Cited

U.S. PATENT DOCUMENTS 5,683,890 A * 11/1997 Germond et al. ............ 435/69.1
6,403,082 B1 * 6/2002 Stiles et al. .................. 424/93.2

OTHER PUBLICATIONS

Bergey's Manual of Systematic Bacteriology. 1986. vol. 2, pp. 1059-1062.*
Bergey's Manual of Determinative Bacteriology. 1994, 9$^{th}$ edition, pp. 528, 538 and 539.*
Vancanneyt, Marc et al., "Intraspecies Genomic Groups in *Enterococcus faecium* and Their Correlation with Origin and Pathogenicity," *Applied and Environmental Microbiology*, Mar. 2002, vol. 68, No. 3, pp. 1381-1391.
Folli, Claudia et al., "Purification of Bacteriocin AS48 from an *Enterococcus faecium* Strain and Analysis of the Gene Cluster Involved in its Production," *FEMS Microbiology Letters*, 2003, vol. 221, pp. 143-149.
Del Campo, Rosa et al., "Bacteriocin Production in Vancomycin-Resistant and Vancomycin-Susceptible *Enterococcus* Isolates of Different Origins," *Antimicrobial Agents and Chemotherapy*, Mar. 2001, vol. 45, No. 3, pp. 905-912.
Laukova, A. et al., "Inhibition of *Salmonella enterica* serovar Dusseldorf by enterocin A in gnotobiotic Japanese quails," 2004, vol. 49, No. 2, pp. 47-51.
Laukova, A. et al., "Antagonistic effect of enterocin CCM 4231 from *Enterococcus faecium* on "bryndza," a traditional Slovak dairy product from sheep milk," *Microbiological Research*, Apr. 2001, vol. 156, No. 1, pp. 31-34.
Aymerich, Teresa et al., "Biochemical and Genetic Characterization of Enterocin A from *Enterococcus faecium*, a New Antilisterial Bacteriocin in the Pediocin Family of Bacteriocins," May 1996, vol. 62, No. 5, pp. 1676-1682.
Strompfova, V. et al., "Effect of Bacteriocin-Like Substance Produce by *Enterococcus faecium* EF55 on the Composition of Avian Gastrointestinal Microflora," 2003, vol. 72, pp. 559-564.
"*Enterococci* in Foods Functional and Safety Aspects," *Programme and Book of Abstracts*, May 30-31, 2002, Berlin, Germany.
Drake, David et al., "Specificity of the Glucan-Binding Lectin of *Streptococcus cricetus*," *Infection and Immunity*, Aug. 1998, vol. 56, pp. 1864-1872.

* cited by examiner

*Primary Examiner* — Vera Afremova
(74) *Attorney, Agent, or Firm* — John D. Fado; Gail E. Poulos (57) ABSTRACT

Novel *Enterococcus* and *Streptococcus* bacteriocins produced by novel *Enterococcus* and *Streptococcus* strains are used for at least reducing the levels of colonization by at least one target bacteria in animals, especially poultry.

7 Claims, 2 Drawing Sheets

SEQUENCE LISTING

<160> NUMBER OF SEQ ID NOS: 2

<210> SEQ ID NO 1
<211> LENGTH: 39
<212> TYPE: PRT
<213> ORGANISM: Enterococcus faecium

<400> SEQUENCE: 1

Thr Thr Lys Asn Tyr Gly Asn Gly Val Cys Asn Ser Val Asn Trp Cys
1               5                   10                  15

Gln Cys Gly Asn Val Trp Ala Ser Cys Asn Leu Ala Thr Gly Cys Ala
            20                  25                  30

Ala Trp Leu Cys Lys Leu Ala
        35

<210> SEQ ID NO 2
<211> LENGTH: 62
<212> TYPE: PRT
<213> ORGANISM: Streptococcus cricetus

<400> SEQUENCE: 2

Asn Arg Trp Tyr Cys Asn Ser Ala Ala Gly Val Gly Ala Ala
1               5                   10                  15

Val Cys Gly Leu Ala Gly Tyr Val Gly Glu Ala Lys Glu Asn Ile Ala
            20                  25                  30

Gly Glu Val Arg Lys Gly Trp Gly Met Ala Gly Gly Phe Thr His Asn
        35                  40                  45

```
Lys Ala Cys Lys Ser Phe Pro Gly Ser Gly Trp Ala Ser Gly
 50              55              60
```

ENTEROCOCCUS AND STREPTOCOCCUS STRAINS AND BACTERIOCINS

BACKGROUND OF THE INVENTION

1. Field of the Invention

This invention relates to the control of disease in animals, especially poultry, through the use of novel bacteriocin-producing *Enterococcus* strains and/or novel bacteriocins produced by these strains. It also relates to novel bacteriocins, amino acid sequences, of the novel bacteriocins, to the strains of *Enterococcus* producing the novel bacteriocins and to inducer strains of *Pediococcus*. Furthermore, the invention relates to therapeutic compositions containing the novel bacteriocins and/or the strains of *Enterococcus* producing them and to uses of the therapeutic compositions.

2. Description of the Related Art

The consumption of improperly prepared poultry products has resulted in human intestinal diseases. It has long been recognized that *Salmonella* spp. are causative agents of such diseases and more recently, *Campylobacter* spp., especially *Campylobacter jejuni*, has also been implicated. Both microorganisms may colonize poultry gastrointestinal tracts without any deleterious effects on the birds, and although some colonized birds can be detected, asymptomatic carriers can freely spread the microorganisms during production and processing, resulting in further contamination of both live birds and carcasses. Poultry serves as the primary reservoir for *Salmonella* and *Campylobacter* in the food supply (Jones et al., Journal of Food Protection, Volume 54, No. 7, 502-507, July, 1991). Prevention of colonization in live poultry during grow out production may diminish the problem of poultry contamination.

A number of factors contribute to the colonization and continued presence of bacteria within the digestive tract of animals. These factors have been extensively reviewed by Savage (Progress in Food and Nutrition Science, Volume 7, 65-74, 1983). Included among these factors are: (1) Gastric acidity (Gilliland, Journal of Food Production, Volume 42, 164-167, 1979); (2) bile salts (Sharpe & Mattick, Milchwissenschaft, Volume 12, 348-349, 1967; Floch et al., American Journal of Clinical Nutrition, Volume 25, 1418-1426, 1972; Lewis & Gorbach, Archives of Internal Medicine, Volume 130, 545-549, 1972; Gilliland and Speck, Journal of Food Protection, Volume 40, 820-823, 1977); Hugdahl et al., Infection and Immunity, Volume 56, 1560-1566, 1988); (3) peristalsis; (4) digestive enzymes (Marmur, Journal of Molecular Biology, Volume 3, 208-218, 1961); (5) immune response; and (6) indigenous microorganisms and the antibacterial compounds which they produce. The first four factors are dependent on the phenotype of the host and may not be practically controllable variables. The immune response in the gastrointestinal (GI) tract is not easily modulated. The factors involving indigenous microorganisms and their metabolites are dependent on the normal flora of the GI tract.

One potential approach to control *Campylobacter* and/or *Salmonella* colonization is through the use of competitive exclusion (CE). Nurmi and Rantala (Nature, Volume 241, 210-211, 1973) demonstrated effective control of *Salmonella* infection by gavaging bacteria from healthy poultry intestinal materials into young chicks whose microflora had not yet been established, against *Salmonella* colonization. Administration of undefined CE preparations to chicks speeds the maturation of gut flora in newly-hatched birds and provides a substitute for the natural process of transmission of microflora from the adult hen to its offspring. Results from laboratory and field investigations provide evidence of benefits in *Campylobacter* control through administering normal microflora to chickens; decreased frequency of *Campylobacter*-infected flocks (Mulder and Bolder, IN: Colonization Control of human bacterial enteropathogens in poultry; L. C. Blankenship (ed.), Academic Press, San Diego, Calif., 359-363, 1991) and reduced levels of *Campylobacter jejuni* (*C. jejuni*) in the feces of colonized birds has been reported (Stern, Poultry Science, Volume 73, 402-407, 1994).

Schoeni and Wong (Appl. Environ. Microbiol., Volume 60, 1191-1197, 1994) reported a significant reduction in broiler colonization by *C. jejuni* through the application of carbohydrate supplements together with three identified antagonists: *Citrobacter diversus* 22, *Klebsiella pneumoniae* 23, and *Escherichia coli* 25. There is also evidence of a significant decrease of *C. jejuni* in intestinal samples from infected broilers after treatment with poultry-isolated cultures of *Lactobacillus acidophilus* and *Streptococcus faecium* (Morishita et al., Avian Diseases, Volume 41, 850-855, 1997).

Snoeyenbos et al. (U.S. Pat. No. 4,335,107, June, 1982) developed a competitive exclusion (CE) microflora technique for preventing *Salmonella* colonization by lyophilizing fecal droppings and culturing this preparation anaerobically. Mikola et al. (U.S. Pat. No. 4,657,762, April, 1987) used intestinal fecal and cecal contents as a source of CE microflora for preventing *Salmonella* colonization. Stern et al. (U.S. Pat. No. 5,451,400, September 1995, and U.S. Pat. No. 6,241,335, April 2001) disclose a mucosal CE composition for protection of poultry and livestock against colonizations by *Salmonella* and *Campylobacter* where the mucin layer of prewashed caeca is scraped and the scrapings, kept in an oxygen-free environment, are cultured anaerobically. Nisbet et al. (U.S. Pat. No. 5,478,557, December, 1996) disclose a defined probiotic that can be obtained from a variety of domestic animals which is obtained by continuous culture of a batch culture produced directly from fecal droppings, cecal and/or large intestine contents of the adult target animal.

Microorganisms produce a variety of compounds which demonstrate anti-bacterial properties. One group of these compounds, the bacteriocins, consists of bactericidal proteins with a mechanism of action similar to ionophore antibiotics. Bacteriocins are often active against species which are closely related to the producer. Their widespread occurrence in bacterial species isolated from complex microbial communities such as the intestinal tract, the oral or other epithelial surfaces, suggests that bacteriocins may have a regulatory role in terms of population dynamics within bacterial ecosystems. Bacteriocins are defined as compounds produced by bacteria that have a biologically active protein moiety and bactericidal action (Tagg et al., Bacteriological Reviews, Volume 40, 722-256, 1976). Other characteristics may include: (1) a narrow inhibitory spectrum of activity centered about closely related species; (2) attachment to specific cell receptors; and (3) plasmid-borne genetic determinants of bacteriocin production and of host cell bacteriocin immunity. Incompletely defined antagonistic substances have been termed "bacteriocin-like substances". Some bacteriocins effective against Gram-positive bacteria, in contrast to Gram-negative bacteria, have wider spectrum of activity. It has been suggested that the term bacteriocin, when used to describe inhibitory agents produced by Gram-positive bacteria, should meet the minimum criteria of (1) being a peptide and (2) possessing bactericidal activity (Tagg et al., supra).

Lactic acid bacteria are among the most important probiotic microorganisms. They are Gram-positive, nonsporing, catalase-negative organisms devoid of cytochromes. They are anaerobic but are aerotoleratant, fastidious, acid-tolerant, and strictly fermentative with lactic acid as the major end-product of sugar fermentation. Lactic acid producing bacteria include *Lactobacillus* species, *Bifidobacterium* species, *Enterococcus faecalis*, *Enterococcus faecium*, *Lactococcus lactic*, *Streptococcus cricetus*, *Leuconostoc mesenteroides*, *Pediococcus acidilactici*, *Sporolactobacillus inulinus*, *Streptococcus thermophilus*, etc. These species are of particular interest in terms of widespread occurrence of bacteriocins within the group and are also in wide use throughout the fermented dairy, food and meat processing industries. Their role in the preservation and flavor characteristics of foods has been well documented. Most of the bacteriocins produced by this group are active only against other lactic acid bacteria, but several display anti-bacterial activity towards more phylogenetically distant Gram-positive bacteria, and under certain conditions, Gram-negative bacteria.

*Lactobacilli* have been extensively studied for production of antagonists. These include the well characterized bacteriocins (DeKlerk, Nature, Volume 214, 609, 1967; Upreti and Hinsdill, Anticmicrob. Agents Chemother., Volume 7, 139-145, 1975; Barefoot and Klaenhammer, Antimicrob. Agents Chemother., Volume 45, 1808-1815, 1983; Joerger and Klaenhammer, Journal of Bacteriology, Volume 167, 439-446, 1986), potential bacteriocin-like substances (Vincent et al., Journal of Bacterioll., Volume 78, 479, 1959), and other antagonists not necessarily related to bacteriocins (Vakil and Shahani, Bacteriology, Proc. 9, 1965; Hamdan and Mikolajcik, Journal of Antibiotics, Volume 8, 631-636, 1974; Mikolajcik and Hamdan, Cultured Dairy Products, Page 10, 1975; and Shahani et al., Cultured Dairy Products Journal, Volume 11, 14-17, 1976).

Klaenhammer (FEMS, Microbiol. Rev., Volume 12, 39-86, 1993) has classified the lactic acid bacteria bacteriocins known to date into four major groups:

Group I: Lantibiotics which are small peptides of <5 kDa containing the unusual amino acids lanthionine and β-methyl lanthionine. These are of particular interest in that they have very broad spectra of activity relative to other bacteriocins. Examples include Nisin, Nisin Z, carnocin U 149, lacticin 481, and lactocin 5.

Group II-Small non-lanthionine containing peptides: a heterogeneous group of small peptides of <10 kDa. This group includes peptides active against *Listeria* spp.

Group III-Large heat labile proteins of >30 kDa. An example is Helveticin.

Group IV-Complex bacteriocins-proteins containing additional moieties such as lipids and carbohydrates.

Raczek (United States Patent Application US2002/0176910, published Nov. 28, 2002) discloses the use of a composition that contains live or dead microorganisms which secrete bacteriocins, or the bacteriocins themselves or in combinations thereof, for use with feedstuffs for agricultural livestock.

Various bacteriocin-producing *Enterococcus* and *Streptococcus* species and their bacteriocins have been described in the related art. However, the present invention provides novel compositions containing at least one novel strain of an *Enterococcus* or *Streptococcus* and/or at least one novel bacteriocin produced by the novel strains; a method of using the strain and/or bacteriocin, the novel strains, amino acid sequences for the novel bacteriocins, and methods of use, all of which are different from related art strains, bacteriocins, and methods of using.

SUMMARY OF THE INVENTION

It is therefore an object of the present invention to provide at least one novel strain of *Enterococcus* that produce novel bacteriocins.

A further object of the present invention is to provide a novel *Enterococcus durans/faecium/hirae* strain having the identifying characteristics of NRRL-B-30745.

A still further object of the present invention is to provide a novel *Enterococcus durans/faecium/hirae* strain having the identifying characteristics of NRRL B-30746.

Another object of the present invention is to provide novel bacteriocins produced by novel strains of *Enterococcus*.

A still further object of the present invention is to provide a novel bacteriocin 50-52 having an amino acid sequence as set forth in SEQ ID NO 1.

A still further object of the present invention is to provide a novel bacteriocin 760 having an amino acid sequence as set forth in SEQ ID NO 2.

A further object of the present invention is to provide a method for at least reducing the levels of colonization by at least one target bacteria in animals by administering to the animal a therapeutic composition including at least one novel strain of *Enterococcus* or a combination of the novel strains and/or bacteriocins.

A still further object of the present invention is to provide a method for at least reducing levels of colonization by at least one target bacteria in animals by administering to the animal a therapeutic composition including a novel strain of *Enterococcus* having the identifying characteristics of NRRL Deposit No. B-30746, NRRL, No. B-30745, and mixtures there of.

A still further object of the present invention is to provide a method for at least reducing the levels of colonization by at least one target bacteria in animals by administering to the animal a therapeutic composition including a novel bacteriocin 50-52 having an amino acid sequence as set forth in SEQ ID NO 1.

A still further object of the present invention is to provide a method for at least reducing the levels of colonization by at least one target bacteria in animals by administering to the animal a therapeutic composition including a novel bacteriocin 760 having an amino acid sequence as set forth in SEQ ID NO 2.

Another object of the present invention is to provide a method for at least reducing the levels of colonization by at least reducing the levels of colonization by at least one target bacteria in an animal by administering to the animal a therapeutic composition comprising a bacteriocin produced by a novel strain of *Enterococcus* having the identifying characteristics of NRRL B-30746, NRRL B-30745, and mixtures thereof.

Another object of the present invention is to provide an inducer strain of *Pediococcus* which increases production of bacteriocins by producer strains.

A further object of the present invention is to provide an inducer strain of *Pediococcus pentosaceus* having the identifying characteristics of NRRL B-30744.

A still further object of the present invention is to provide a method for increasing the production of bacteriocins by producer strains wherein the producer strains are co-cultured with an inducer strain of *Pediococcus*.

A further object of the present invention is to provide a method for increasing the production of bacteriocins by producer strains wherein said producer strains are co-cultured with a *Pediococcus* strain having the identifying characteristics of NRRL B-30744.

A still further object of the present invention is to provide a method for purifying bacteriocins that includes harvesting the culture fluid and the cells as separate samples, isolating the bacteriocin that has adsorbed onto the cell surface of both the producer and the inducer strains by elution with phosphate buffer containing sodium chloride followed by a one step ion-exchange chromatography isolation of the bacteriocin in culture fluid by hydrophobic interaction chromatography.

Further objects and advantages of the invention will become apparent from the following description.

Deposit of the Microorganisms

*Enterococcus durans/faecium/hirae*, designated NRRL B-30745 (Strain 760); *Enterococcus durans/faecium/hirae*, designated NRRL B-30746 (strain 50-52); and *Pediococcus penosaceus*, designated NRRL B-30744 (Strain 320) have been deposited under the provisions of the Budapest Treaty on May 3, 2004 with the USDA Agricultural Research Service Patent Culture Collection (National Center for Agricultural Utilization Research, 1815 N. University Street, Peoria, Ill. 61604).

DETAILED DESCRIPTION OF THE INVENTION

The importance of enteric infections in humans has been increasingly well recognized. The relationship of poultry contamination and human infection is well documented. The ability to diminish this health hazard by interventions at poultry processing plants is also well known. During broiler production and processing, fecal materials containing pathogens are transferred onto meat and persist in the food processing kitchens.

Metabolites of competing organisms may contribute to the control of pathogens such as *Campylobacter jejuni* and *Salmonella*. The novel antagonistic strains were isolated from cecal and crop mucosal surfaces of broilers. The native components of the characterized antagonists are low molecular weight peptides, bacteriocins, which have a wide spectrum of antagonistic activity.

The present invention provides novel *Enterococcus* strains a novel *Pediococcus* strain, novel bacteriocins, amino acid sequences of said bacteriocins, therapeutic compositions containing the novel bacteriocins and/or strains producing them, and methods for using the novel therapeutic compositions. The present invention also provides a method for production and purification of the novel bacteriocins.

*Enterococcus durans/faecium/hirae* NRRL B-30746, is a faculatative aerobe with gram-positive cocci, and is capable of growth at about 37° C. The strain grows on nutrient or plate count agar producing irregular-shaped edges. The colonies are about 2 mm in diameter after microaerophilic cultivation for about 24 hours at about 37° C.

*Enterococcus durans/faecium/hirae*, NRRO B-30745, is a facultative aerobe with gram-positive cocci, and is capable of growth at about 37° C. The strain grows on nutrient or plate count agar producing reglar-shaped edges. The colonies are about 1 mm in diameter after microaerophilic cultivation for about 24 hours at about 37° C.

Screening of isolated *Enterococcus* strains for the production of bacteriocin activity is performed on nutrient agar seeded with different target bacteria of interest. Other test strains are cultured under aerobic conditions at about 37° C. for about 18-24 hours. *Yersinia enterocolitica* and *Y. pseudotuberculosis* are cultured at about 28° C. under aerobic conditions for about 18-24 hours. Tests for activity against *Campylobacter jejuni* are performed on *C. jejuni* seeded *Campylobacter agar* containing about 5% lysed blood. The use of blood is well within the ordinary skill in the art and includes for example, sheep, horse, etc. Tests for activity against *Campylobacter juejuni* is carried out under microaerobic conditions of about 5% $O_2$, about 10% $CO_2$, and about 85% $N_2$ for about 24-48 hours at about 42° C. Approximately 0.1 ml of the antagonistic bacteria suspended in normal saline is plated onto MRS agar and incubated for about 24-48 hours. MRS agar cubes of about 0.5 $cm^3$ are cut out and transferred onto *Brucella* or *Campylobacter agar* supplemented with lysed blood, about 110 micrograms/ml rifampicin, about 2.4 U/ml of polymyxin, and seeded with about $10^7$ cells of *Campylobacter jejuni*. Plates are incubated at about 42° C., for approximately 24-48 hours under microaerobic conditions. Activity is evaluated by measuring zones of growth inhibition.

Isolates found to be antagonistic are evaluated for bacteriocin production. Crude antimicrobial preparations (CAPs) are prepared by ammonium sulfate precipitation from cultures of antagonistic strains grown in about 10% *Brucella* broth together with a bacteriocin-enhancing amount of *Pediococcus pentosaceus* (Strain 320, NRRL B-30744) used as an inducer, at approximately 37° C. for about 14 hours under aerobic conditions. A bacteriocin-enhancing amount of the inducer is defined as an amount of inducer bacteria required to at least increase the bacteriocin production of a producer strain as compared to the producer strain cultured with out the inducer strain. An example of concentration of inducer to producer strain in co-culture in about 10:1 (inducer:producer) The cultures are then centrifuged at about 2,500×g for about 10 minutes. Antagonistic peptides are isolated from supernatant by a combination of ammonium sulfate precipitation, gel filtration using Superose 12 HR, cation ion exchange chromatography usng Sepharose SP FF. With co-cultures, secreted bacteriocins may adsorb onto the cell surface of both the producer and inducer cells. In order to harvest these bacteriocin, the cell pellet from the centrifugation step is mixed with an eluting buffer that is made up of phosphate buffer with approximately 0.7% NaCl, pH about 8.0. The suspension is mixed and incubated for about 20 minutes followed by centrifugation at about 10,000×g for about 15 minutes. The bacteriocin is isolated from the supernatant by ion-exchange chromatography on Superose SP FF. Molecular weights of the peptides are determined by SDS-PAGE electrophoresis. pIs of the peptides are determined by isoelectric focusing. Amino acid sequences are determined by Edman degradation using, for example, a 491 cLC Automactic Sequencer (Applied Biosystems, Inc.).

For purposes of the present invention, the term "peptide" means a compound of at least two or more amino acids or amino acid analogs. The amino. acids or amino acid analogs may be linked by peptide bonds. In another embodiment, the amino acids may be linked by other bonds, e.g., ester, ether, etc. Peptides can be in any structural configuration including linear, branched, or cyclic configurations. As used herein, the term "amino acids" refers to either natural or synthetic amino acids, including both the D or L optical isomers, and amino acid analogs.

Peptide derivatives and analogs of the present invention include, but are not limited to, those containing, as a primary amino acid sequence, all or part of the amino acid sequence of the peptide including altered sequences in which functionally equivalent amino acid residues are substituted for residues within the sequence resulting in conservative amino acid substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Such alterations will not be expected to significantly affect apparent molecular weight as determined by polyacrylamide gel electrophoresis or isoelectric point. Non-conservative amino acid substitutions may also be introduced to substitute an amino acid with a particularly preferable property. For example, Cys may be introduced at a potential site for disulfide bridges with another Cys. Pro may be introduced because of its particularly planar structure.

The peptides of the present invention can be chemically synthesized. Synthetic peptides can be prepared using the well known techniques of solid phase, liquid phase, or peptide condensation techniques, or any combination thereof, and can include natural and/or synthetic amino acids. Amino acids used for peptide synthesis may be standard Boc($N^\alpha$-amino protected $N^\alpha$-t-butyloxycarbonyl) amino acid resin with the standard deprotecting, neutralization, coupling, and wash protocols of the original solid phase procedure of Merrifield (J. Am. Chem. Soc., Volume 85, 2149-2154, 1963), or the base-labile $N^\alpha$-amino protected 9-fluorenylmethoxycarbonyl (Fmoc) amino acid (Carpino and Han, J. Org. Chem., Volume 37, 3403-3409, 1972). In addition, the method of the present invention can be used with other $N^\alpha$-protecting groups that are familiar to those skilled in the art. Solid phase peptide synthesis may be accomplished by techniques within the ordinary skill in the art (See for example Stewart and Young, Solid Phase Synthesis, Second Edition, Pierce Chemical Co., Rockford, Ill., 1984; Fields and Noble, Int. J. Pept. Protein Res., Volume 35, 161-214, 1990), or by using automated synthesizers.

In accordance with the present invention, the peptides and/or the novel bacterial strains can be administered in a therapeutically acceptable carrier topically, parenterally, transmucosally, such as for example, orally, nasally, rectally, or transdermally. The peptides of the present invention can be modified if necessary to increase the ability of the peptide to cross cellular membranes such as by increasing the hydrophobic nature of the peptide, introducing the peptide as a conjugate to a carrier, such as a ligand to a specific receptor, etc.

The present invention also provides for conjugating a targeting molecule to a peptide of the invention. Targeting molecules for purposes of the present invention mean a molecule which when administered in vivo, localizes to a desired location or locations. In various embodiments of the present invention, the targeting molecule can be a peptide or protein, antibody, lectin, carbohydrate, or steroid. The targeting molecule can be a peptide ligand of a receptor on the target cell or an antibody such as a monoclonal antibody. To facilitate crosslinking the antibody can be reduced to two heavy and light chain hetero-dimers, or the $F(ab')_2$ fragment can be reduced, and crosslinked to the peptide via the reduced sulfhydryl.

Another aspect of the present invention is to provide therapeutic compositions. The compositions may be for oral, nasal, pulmonary administration, injection, etc. The therapeutic compositions include effective amounts of at least one bacteriocin of the present invention and their derivatives and/or at least one novel strain to at least reduce the levels of colonization by at least one target bacteria together with acceptable diluents, preservatives, solubilizers, emulsifiers, adjuvants, and/or carriers. Diluents can include buffers such as Tris-HCl, acetate, phosphate, for example; additives can include detergents and solubilizing agents such as Tween 80, Polysorbate 80, etc., for example; antioxidants include, for example, ascorbic acid, sodium metabisulfite, etc.; preservatives can include, for example, Thimersol, benzyl alcohol, etc.; and bulking substances such as lactose, mannitol, etc.

The therapeutic composition of the present invention can be incorporated into particulate preparation of polymeric compounds such as polyvinylpyrrolidone, polylactic acid, polyglycolic acid, etc., or into liposomes. Liposomal encapsulation includes encapsulation by various polymers. A wide variety of polymeric carriers may be utilized to contain and/or deliver one or more of the therapeutic agents discussed above, including for example both biodegradable and nonbiodegradable compositions. Representative examples of biodegradable compositions include albumin, collagen, gelatin, hyaluronic acid, starch, cellulose (methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(D,L lactide), poly (D,L-lactide-co-glycolide), poly(glycolide), poly(hydroxybutyrate), poly(alkylcarbonate) and poly (orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986).

Representative examples of nondegradable polymers include poly(ethylene-vinyl acetate) ("EVA") copolymers, silicone rubber, acrylic polymers (polyacrylic acid, polymethylacrylic acid, polymethylmethacrylate, polyalkylcynoacrylate), polyethylene, polypropylene, polyamides (nylon 6,6), polyurethane, poly(ester urethanes), poly(ether urethanes), poly(ester-urea), polyethers (poly(ethylene oxide), poly(propylene oxide), Pluronics and poly(tetramethylene glycol)), silicone rubbers and vinyl polymers such as polyvinylpyrrolidone, poly(vinyl alcohol), poly(vinyl acetate phthalate). Polymers may also be developed which are either anionic (e.g., alginate, carrageenin, carboxymethyl cellulose and poly(acrylic acid), or cationic (e.g., chitosan, poly-L-lysine, polyethylenimine, and poly (allyl amine)) (see generally, Dunn et al., J. Applied Polymer Sci. 50:353-365, 1993; Cascone et al., J. Materials Sci.: Materials in Medicine 5:770-774, 1994; Shiraishi et al., Biol. Pharm. Bull. 16(11):1164-1168, 1993; Thacharodi and Rao, Int'l J. Pharm. 120:115-118, 1995; Miyazaki et al., Int'l J. Pharm. 118:257-263, 1995).

Polymeric carriers can be fashioned in a variety of forms, with desired release characteristics and/or with specific desired properties. For example, polymeric carriers may be fashioned to release a therapeutic agent upon exposure to a specific triggering event such as pH (see e.g., Heller et al., "Chemically Self-Regulated Drug Delivery Systems," in Polymers in Medicine III, Elsevier Science Publishers B. V., Amsterdam, 1988, pp. 175-188; Kang et al., J. Applied Polymer Sci. 48:343-354, 1993; Dong et al., J. Controlled Release 19:171-178, 1992; Dong and Hoffman, J. Controlled Release 15:141-152, 1991; Kim et al., J. Controlled Release 28:143-152, 1994; Cornejo-Bravo et al., J. Controlled Release 33:223-229, 1995; Wu and Lee, Pharm. Res. 10(10):1544-1547, 1993; Serres et al., Pharm. Res. 13(2):196-201, 1996; Peppas, "Fundamentals of pH- and Temperature-Sensitive Delivery Systems," in Gurny et al. (eds.), Pulsatile Drug Delivery, Wissenschaftliche Verlagsgesellschaft GmbH, Stuttgart, 1993, pp. 41-55; Doelker, "Cellulose Derivatives," 1993, in Peppas and Langer (eds.), Biopolymers I, Springer-Verlag, Berlin). Representative examples of pH-sensitive polymers include poly(acrylic acid) and its derivatives (including for example, homopolymers such as poly(aminocarboxylic acid); poly(acrylic acid); poly (methyl acrylic acid), copolymers of such homopolymers, and copolymers of poly (acrylic acid) and acrylmonomers such as those discussed above. Other pH sensitive polymers include polysaccharides such as cellulose acetate phthalate; hydroxypropylmethylcellulose phthalate; hydroxypropylmethylcellulose acetate succinate; cellulose acetate trimellilate; and chitosan. Yet other pH sensitive polymers include any mixture of a pH sensitive polymer and a water soluble polymer.

Likewise, polymeric carriers can be fashioned which are temperature sensitive (see e.g., Chen et al., "Novel Hydrogels of a Temperature-Sensitive Pluronic Grafted to a Bioadhesive Polyacrylic Acid Backbone for Vaginal Drug Delivery," in Proceed. Intern. Symp. Control. Rel. Bioact. Mater. 22:167-168, Controlled Release Society, Inc., 1995; Okano, "Molecular Design of Stimuli-Responsive Hydrogels for Temporal Controlled Drug Delivery," in Proceed. Intern. Symp. Control. Rel. Bioact. Mater. 22:111-112, Controlled Release Society, Inc., 1995; Johnston et al., Pharm. Res. 9(3):425-433, 1992; Tung, Int'l J. Pharm. 107:85-90, 1994; Harsh and Gehrke, J. Controlled Release 17:175-186, 1991; Bae et al., Pharm. Res. 8(4):531-537, 1991; Dinarvand and D'Emanuele, J. Controlled Release 36:221-227, 1995; Yu and Grainger, "Novel Thermo-sensitive Amphiphilic Gels: Poly N-isopropylacrylamide-co-sodium acrylate-co-n-N-alkylacrylamide Network Synthesis and Physicochemical Characterization," Dept. of Chemical & Biological Sci., Oregon Graduate Institute of Science & Technology, Beaverton, Oreg., pp. 820-821; Zhou and Smid, "Physical Hydrogels of Associative Star Polymers," Polymer Research Institute, Dept. of Chemistry, College of Environmental Science and Forestry, State Univ. of New York, Syracuse, N.Y., pp. 822-823; Hoffman et al., "Characterizing Pore Sizes and Water 'Structure' in Stimuli-Responsive Hydrogels," Center for Bioengineering, Univ. of Washington, Seattle, Wash., p. 828; Yu and Grainger, "Thermo-sensitive Swelling Behavior in Crosslinked N-isopropylacrylamide Networks: Cationic, Anionic and Ampholytic Hydrogels," Dept. of Chemical & Biological Sci., Oregon Graduate Institute of Science & Technology, Beaverton, Oreg., pp. 829-830; Kim et al., Pharm. Res. 9(3):283-290, 1992; Bae et al., Pharm. Res. 8(5):624-628, 1991; Kono et al., J. Controlled Release 30:69-75, 1994; Yoshida et al., J. Controlled Release 32:97-102, 1994; Okano et al., J. Controlled Release 36:125-133, 1995; Chun and Kim, J. Controlled Release 38:39-47, 1996; D'Emanuele and Dinarvand, Int'l J. Pharm. 118:237-242, 1995; Katono et al., J. Controlled Release 16:215-228, 1991; Hoffman, "Thermally Reversible Hydrogels Containing Biologically Active Species," in Migliaresi et al. (eds.), Polymers in Medicine III, Elsevier Science Publishers B. V., Amsterdam, 1988, pp. 161-167; Hoffman, "Applications of Thermally Reversible Polymers and Hydrogels in Therapeutics and Diagnostics," in Third International Symposium on Recent Advances in Drug Delivery Systems, Salt Lake City, Utah, Feb. 24-27, 1987, pp. 297-305; Gutowska et al., J. Controlled Release 22:95-104, 1992; Palasis and Gehrke, J. Controlled Release 18:1-12, 1992; Paavola et al., Pharm. Res. 12(12):1997-2002, 1995).

Representative examples of thermogelling polymers, and their gelatin temperature (LCST (.degree. C.)) include homopolymers such as poly(N-methyl-N-n-propylacrylamide), 19.8; poly(N-n-propylacrylamide), 21.5; poly (N-methyl-N-isopropylacrylamide), 22.3; poly(N-n-propylmethacrylamide), 28.0; poly(N-isopropylacrylamide), 30.9; poly(N, n-diethylacrylamide), 32.0; poly(N-isopropylmethacrylamide), 44.0; poly (N-cyclopropylacrylamide), 45.5; poly(N-ethylmethyacrylamide), 50.0; poly(N-methyl-N-ethylacrylamide), 56.0; poly(N-cyclopropylmethacrylamide), 59.0; poly(N-ethylacrylamide), 72.0. Moreover thermogelling polymers may be made by preparing copolymers between (among) monomers of the above, or by combining such homopolymers with other water soluble polymers such as acrylmonomers (e.g., acrylic acid and derivatives thereof such as methylacrylic acid, acrylate and derivatives thereof such as butyl methacrylate, acrylamide, and N-n-butyl acrylamide). Other representative examples of thermogelling polymers include cellulose ether derivatives such as hydroxypropyl cellulose, 41.degree. C.; methyl cellulose, 55.degree. C.; hydroxypropylmethyl cellulose, 66.degree. C.; and ethylhydroxyethyl cellulose, and Pluronics such as F-127, 10-15.degree. C.; L-122, 19.degree. C.; L-92, 26.degree. C.; L-81, 20.degree. C.; and L-61, 24.degree. C.

A wide variety of forms may be fashioned by the polymeric carriers of the present invention, including for example, rod-shaped devices, pellets, slabs, or capsules (see e.g., Goodell et al., Am. J. Hosp. Pharm. 43:1454-1461, 1986; Langer et al., "Controlled release of macromolecules from polymers", in Biomedical Polymers, Polymeric Materials and Pharmaceuticals for Biomedical Use, Goldberg, E. P., Nakagim, A. (eds.) Academic Press, pp. 113-137, 1980; Rhine et al., J. Pharm. Sci. 69:265-270, 1980; Brown et al., J. Pharm. Sci. 72:1181-1185, 1983; and Bawa et al., J. Controlled Release 1:259-267, 1985).

Therapeutic agents may be linked by occlusion in the matrices of the polymer, bound by covalent linkages, or encapsulated in microcapsules. Within certain preferred embodiments of the invention, therapeutic compositions are provided in non-capsular formulations such as microspheres (ranging from nanometers to micrometers in size), pastes and threads of various size, films and sprays.

Another aspect of the present invention is to provide a therapeutic composition and animal feed. The therapeutic composition of the present invention can be encapsulated using a polymeric carrier as described above and then added to a feed by any known means of applying it to feed such as for example, by mechanical mixing, spraying, etc. The therapeutic composition includes, for example, an amount of at least one bacteriocin effective to at least reduce the levels of colonization by at least one target bacteria in an animal, such as for example approximately 0.5 grams of bacteriocin(s)/100 grams, approximately 1.25 grams of a polymeric carrier such as polyvinylpyrrolidone/100 grams, and about 8.6% of a diluent such as water/100 grams mixed with any granular component that is digestable, such as for example, milled maize grain; ground grains such as for example oats, wheat, buckwheat; ground fruits such as for example, pears, etc. The therapeutic composition is then added to any type of animal feed in amounts effective to at least reduce the levels of colonization of at least one target bacteria such as for example in ratios of bacteriocin to feed of about 1:10 to about 1:100. For purposes of the present invention, examples of animal feed include green fodder, silages, dried green fodder, roots, tubers, fleshy fruits, grains, seeds, brewer's grains, pomace, brewer's yeast, distillation residues, milling byproducts, byproducts of the production of sugar, starch or oil production, and various food wastes. The product can be added to the animal feedstuffs for cattle, poultry, rabbit, pig, or sheep rearing, etc. It can be mixed with other feed additives for these stock.

The following examples are intended only to further illustrate the invention and are not intended to limit the scope of the invention as defined by the claims.

EXAMPLE 1

Two novel antagonistic strains, *Enterococcus durans/faecium/hirae* Strain 50-52 (NRRL B-30746) and strain 760 (NRRL B-30745) were isolated from mucous surfaces of about 1.0 gram of the ceca of broilers which was suspended in about 10 ml of sterile 0.85% w/v saline solution (normal saline) and heated at about 80° C. for about 15 minutes. Approximately 0.10 ml of about 1:50 and 1:2,500 suspensions was spread plated onto either plate count agar or MRS agar. Plates were incubated at about 37° C. for about 24 hours under microaerobic conditions. Colonies with different morphology were streaked onto MRS agar. These cultures were incubated under microaerobic conditions for about 24 hours at about 37° C.

Strain 760 was grown at approximately 37° C. for about 24 hours on MRS Agar. The strain is a facultative aerobe with gram-positive cocci, is able to grow between approximately 37° C. and 45° C. The strain grows on nutrient agar or plate count agar producing circular regular-shaped, low convex, grayish colonies with wavy margins that are about 2 mm in diameter after aerobic incubation at about 37° C. for about 24 hours. Biochemical properties of strain 760 were determined with system APJ 50 CLH (Bio-Merieux, France). The strain degrades lactose, mannitol, ribose, salicin, sorbitol, trehalose, arabinose, and melibiose. It slightly hydrolyzes raffinose and inulin, and does not hydrolyze arginine and esculine. It is not capable of α and β hemolysis. It does not grow in the presence of about 6.5% sodium chloride. The strain is catalase-negative.

Strain 50-52 was grown on MRS agar at approximately 37° C. for about 24 hours. The strain is a facultative aerobe with gram-positive cocci, is able to grow on nutrient agar or plate count agar producing circular irregular-shaped, low convex, grayish colonies with wavy margins that are about 1 mm in diameter after aerobic incubation at about 37° C. for about 24 hours. Biochemical properties of strain 50-52 were determined with system EN-Coccus test. The strain degrades arginine, arabinose, and mannitol; and does not hydrolyze sorbose, sorbitol, melibiose, raffinose, and meticitose. It grows in the presence of about 6.5% sodium chloride.

Target bacteria, for assessing antagonistic activity of strains 50-52 and 760, included isolates of *Campylobacter jejuni* (*C. jejuni*) NCTC 11168, *S. enteritidis*, and *E. coli* 0157:H7. Cultures of *C. jejuni* were grown on *Brucella* agar or *Campylobacter* agar containing about 5% partially lysed blood at about 42° C. for approximately 24-48 hours under microaerobic conditions of about 5% $O_2$, about 10% $CO_2$, and about 85% $N_2$. The other strains were cultured on nutrient agar at about 37° C., for about 24 hours. Antagonistic activity of the isolates against *Campylobacter* was evaluated. Approximately 0.2 ml of the suspensions in normal saline was plated onto MRS agar and incubated at about 37° C. for about 24 hours. MRS agar cubes of about 0.5 cm$^3$ were cut out and transferred onto *brucella* agar or *Campylobacter* agar supplemented with about 5%-10% partially lysed blood, about 10 micrograms/ml rifampicin, and about 2.5 u/ml of polymyxin and inoculated with approximately 10$^7$ cells of *Campylobacter jejuni* per plate. Plates were incubated at about 42° C. for approximately 24 to 48 hours under microaerobic conditions as described above. Antagonistic activity was evaluated by measuring the size of the diameter of the zones of *C. jejuni* inhibition.

EXAMPLE 2

Crude antimicrobial preparations were extracted from cultures of the two antagonistic strains: *Enterococcus durans/faecium/hirae* 50-52 and *Enterococcus durans/faecium/hirae* 760. Antagonists were grown in about 250 ml of 10% *Brucella* broth together with inducer strain *Pediococcus pentosaceus* Strain 320 (NRRL B-30744, supra) at about 37° C. for about 14 hours under aerobic conditions. Concentration of producer strain was about 10$^6$ CFU/ml and for inducer strain about 10$^7$ CFU/ml. The resulting cultures were centrifuged at approximately 2,500×g for about 10 minutes, removing most of the viable cells. The decanted supernatant was mixed with about 60% saturated ammonium sulfate and incubated at about 4° C. for about 24 hours to precipitate the bacteriocin compounds. Following centrifugation at approximately 10,000×g for about 20 minutes, the sediment was resuspended in approximately 1.5 ml of about 10 mM phosphate sodium buffer, pH about 7.0, and dialyzed overnight against approximately 2.5 liters of the same buffer. The solution was designated a crude antimicrobial preparation (CAP). Each sample of the preparation was sterilized by passing through a 0.22 micron-pore filter (Millipore, Bedford, MA, USA). Table 1 shows bacteriocin production with and without the use of the inducer strain.

TABLE 1

Bacteriocin production with and without the use of inducer strain *Lactococcus lactis* strain 320.

| | Bacteriocin 760 | | | | | Bacteriocin 50-52 | | | | |
|---|---|---|---|---|---|---|---|---|---|---|
| Method of Cultivation | Amount of protein mg | Activity AU/ml | Specific Activity AU/mg | SDS-PAGE | IEF | Amount of Protein mg | Activity AU/ml | Specific Activity AU/mg | SDS-PAGE | IEF |
| With Inducer strain | 0.18 | 51,200 | 284,444 | 5.5 kD | 9.5 | 0.04 | 12,800 | 320,000 | 3.9 kD | 8.4 |
| Without Inducer strain | 0.04 | 6,400 | 160,000 | 5.5 kD | 9.5 | 0.015 | 3,200 | 213,333 | 3.9 kD | 8.4 |

EXAMPLE 3

The spectrum of antimicrobial activity of the CAPs was determined using a spot test. Approximately 1 ml of sterile crude antimicrobial preparations (CAP), obtained as in Example 2 above, were diluted with approximately 1 ml of phosphate-sodium buffer (pH about 7.0) and sterilized as above in Example 2. Approximately 10 microliters of each sample were plated onto blood-supplemented *Campylobacter agar* or Nutrient agar (MPA or Meta Peptone Agar) previously seeded with cells of target bacteria. Plates containing cultures of *C. jejuni* were grown at about 42° C. under microaerobic conditions, *Y. enterocolitica* and *Y. pseudotuberculosis* were cultured aerobically at about 28° C., and other bacterial strains were incubated aerobically at about 37° C. for about 24 or 48 hours. Identification was based on inhibition areas produced by the target bacteria. Activity of CAP was expressed in arbitrary units (AU) per one milliliter of the preparation at which a visible zone of inhibition of the growth of culture appears (Henderson et al., Archives of Biochemistry and Biophysics, Volume 295, 5-12, 1992; herein incorporated by reference). All experiments were conducted in duplicate. See Table 2 in Example 4 below.

EXAMPLE 4

CAPs and bacteriocins were electrophoresed in about 15% agarose gel weight, about 1% SDS (9×12 cm) in Tri-glycine buffer. After electrophoresis at about 100 mA for approximately 4 hours, gels were fixed with a solution containing approximately 15% ethanol and approximately 1% acetic acid. The gels were then washed with distilled water for approximately 4 hours. To determine molecular weights of protein fractions, the gel was stained with a solution containing approximately 0.21% Coomassi Blue G-250, about 40% ethanol, and about 7% acetic acid. Washed gels were tested against three target bacteria, *C. jejuni* NCTC 11168, *E. coli* 0157:H7 904, and *S. enteritidis* 204 by the method of Bhunia et al. (Journal of Industrial Microbiology, Volume 2, 319-322, 1987; herein incorporated by reference). The gels were placed in Petri dishes, covered with 5% blood-semi-solid *Campylobacter* agar (about 0.75%) or semi-solid MPA, and seeded with cells of the test strains. Plates containing *C. jejuni* were incubated at about 42° C. for approximately 48 hours under microaerobic conditions, *E. coli* 0157:H7 and *S. enteriditis* at about 37° C. for approximately 24 hours. Assessment was based on visualization of zones of the inhibited growth of the test strains in the presence of bacteriocins.

Figure 1:
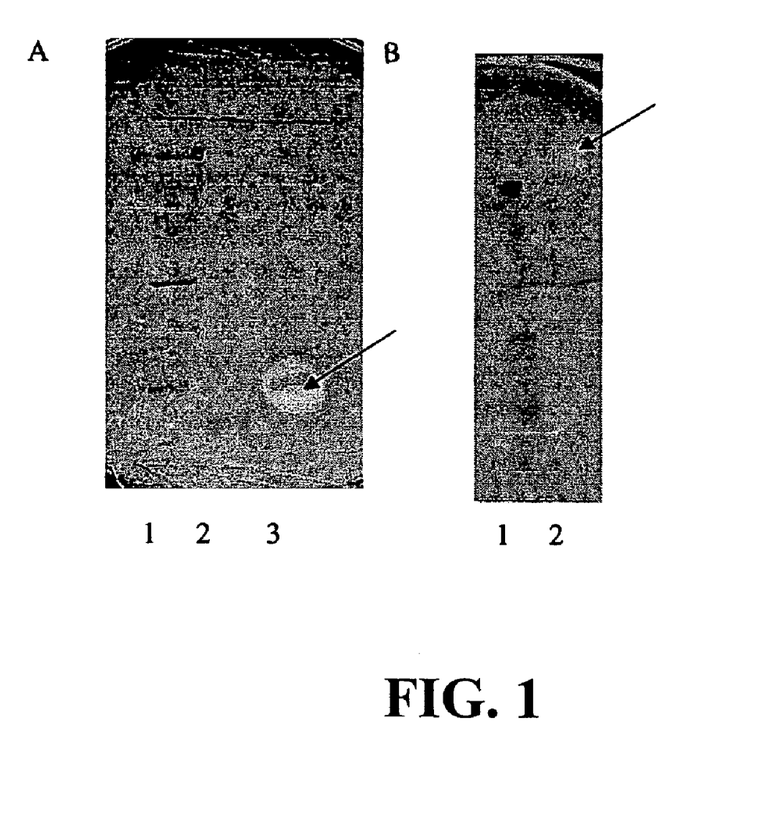
FIGS. 1A-1B are photographs showing direct detection of bacteriocin 760 after SDS-PAGE (1A) and isoelectric focusing (1B).
Figure 2:
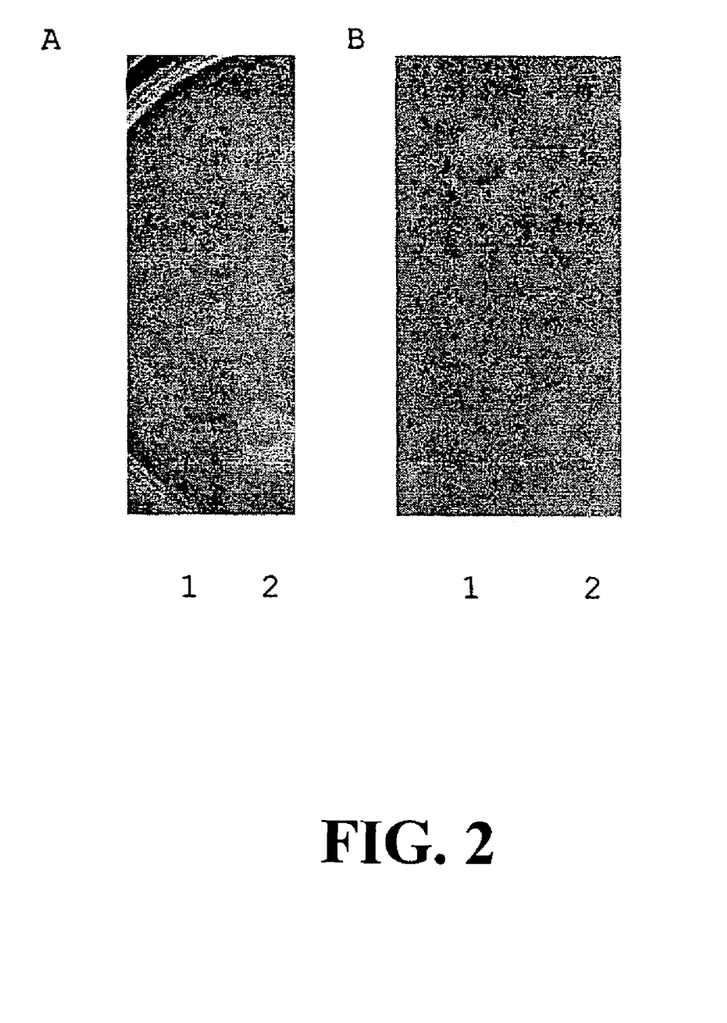
FIGS. 2A and 2B are photographs showing direct detection of bacteriocin 50-52 after SDS-PAGE (2A) and isoelectric focusing (2B).

Isoelectrofocusing identified two distinct fractions which differed in isoelectric points (pI: CAP 760, contained fractions with pI=about 9.2 and about 9.5. CAP 50-52 contained fractions with pI=about 7.7 and 8.4. Antagonistic activity to *C. jejuni* was observed in the fraction with pI=about 9.5 in preparation 760, while in preparation 50-52 this inhibition was observed in the fraction with pI=about 8.4 (FIGS. 1A-B and 2A-B, Table 1 below).

The gels overlaid with *Campylobacter jejuni* were used to determine which band(s) correspond to the antimicrobial activity, the molecular weight and the isoelectric point. FIGS. 1A and 1B for Bacteriocin 760, show the molecular weight of the active fraction (1A) and isoelectric point for the active fraction (1B). The gels were overlaid with *Campylobacter jejuni* to determine the antimicrobial activity, molecular weight, and isoelectric point. In FIG. 1A, lane 1 shows molecular weight markers LMW range of 14,400-94,000 (Amersham Pharmacia Biotech): 14,000; 20,100; 30,000; 43,000; 67,000; and 94,000 Da. In Lane 2 are molecular weight markers for insulin, chain β (Sigma, USA):3,500 Da. Lane 3 shows pure bacteriocin 760 which corresponds to the antimicrobial activity, the zone of growth inhibition (arrow) has a mass of about 5,500 Da. FIG. 1B, lane 1 shows pI standards (Protein Test Mixture, pI Marker Proteins, Serva). Lane 2 shows pure bacteriocin 760 which corresponds to the antimicrobial activity, the zone of growth inhibition (arrow) had a pI of about 9.5. The other bands did not show antimicrobial activity.

FIGS. 2A and 2B show direct detection of bacteriocin 50-52 using SDS-PAGE (2A) and isoelectric focusing (2B). The gel was overlaid with *Campylobacter jejuni* to determine which band(s) correspond to the antimicrobial activity and molecular weight as shown in FIG. 2A. Lane 1 shows Molecular Weight Markers LMW Range 1,600-26,000 (Amersham Pharmacia Biotech): 1,600; 3,500; 6,500; 14,200; 17,000; and 26,000 Da. The band in lane 2 which contains pure bacteriocin 50-52 corresponds to the antimicrobial activity, the zone of growth inhibition and had a mass of about 3,900 Da. FIG. 2B, lane 1 contained pI standards (Protein Test Mixture, pI Marker Proteins, Serva). The band in lane 2 (pure bacteriocin 50-52), which corresponds to the antimicrobial activity, the zone of growth inhibition (arrow) had a pI of about 8.4. The other bands did not show antimicrobial activity.

Specimens of bacteriocins were placed on IEF gels (pH approximately 4.4-10.0) (Novex, San Diego, Calif.). The gels were run at about 100V for about 1 hour, 200V for about 2 hour, and 500V for about 30 minutes in XCM II™ Mini-Cell (Novex). Gels were washed with distilled water for about 4 hours without fixation followed by staining with Coomassie Blue G-250 to determine isoelectric points (pI) of the bacteriocins and their ability to inhibit the growth of the test strains as presented in FIGS. 1 and 2 and in Table 2.

TABLE 2

Antimicrobial activity of crude antimicrobial preparations (CAP) of bacteriocins evaluated by methods of a spot test, SDS-PAGE, and Isoelectrofocusing(IEF).

| Bacteriocin | Test strains | Inhibiting activity in Spot Test (AU/ml) | Inhibiting Activity measured by SDS-PAGE | Inhibiting Activity measured by IEF |
|---|---|---|---|---|
| 760 | *C. jejuni* NCTC 11168 | 51,200 | M.W. 5.5 kDa | band 1 pI = 9.5 |
|  | *S. enteritidis* 204 | 12,800 | M.W. 5.5 kDa | band 1 pI = 9.5 |
|  | *E. coli* O157:H7 904 | 12,800 | M.W. 5.5 kDa | band 1 pI = 9.5 |
| 50-52 | *C. jejuni* ATCC 11168 | 12,800 | M.W. 3.9 kDa | band 1 pI = 8.4 |
|  | *S. enteritidis* 204 | 12,800 | M.W. 3.9 kDa | band 1 pI = 8.4 |
|  | *E. coli* O157:H7 904 | 3,200 | M.W. 3.9 kDa | band 1 pI = 8.4 |

EXAMPLE 5

Producing *Enterococcus durans/faecium/hirae* 50-52 and *Enterococcus durans/faecium/hirae* 760 were simultaneously cultured with an inducing strain of bacteria, *Pediococcus pentosaceus* (strain 320, supra) in Brucella Broth (Difco). Approximately $1.32 \times 10^7$ cells of *Enterococcus durans/faecium/hirae* 50-52 or 760 were placed together with approximately $3.9 \times 10^6$ cells of *Pediococcus pentosaceus* in 250 ml flasks and cultured for about 24 hours. Concentrations of producing and inducing strains were determined every two hours along with the specific activity of the bacteriocin to determine the optimum time for obtaining useable quantities of the bacteriocin. The bacteriocins were isolated and purified by two methods. The first was sedimentation of the bacteriocin using ammonium sulfate followed by three stage chromatography: Gel filtration on Superose 12 HR, ion-exchange chromatography on Superose SPFF, and hydrophobic interaction chromatography on Octyl Sepharose 4 FF. This is Method A.

For Method B, upon simultaneous culture of producer and inducer strains, most of the bacteriocin produced is secreted into the culture fluid. A portion of the bacteriocin will adsorb on both the inducer and producer strain cells. In order to avoid the loss of the adsorbed bacteriocin, the bacteriocin is eluted from the cells. Method B involves two steps: (1) the isolation of bacteriocin from the supernatant of the culture fluid; and (2) the isolation of bacteriocin from the precipitate of cells of both the inducing and producing strains. In step 1, the cultures are harvested and separated by centrifugation at about 10,000 g for about 15 minutes to precipitate the cells. The supernatant is applied to a Octyl Sepharose 4 FF column to recover the bacteriocin. The cell precipitate is used in step 2. The precipitate was suspended in phosphate buffer with about 0.7% NaCl, pH (eluting buffer) and the suspension was mixed and incubated for about 20 minutes. After incubation, the suspension was centrifuged at about 10,000 g for about 15 minutes. The bacteriocin was isolated from the supernatant using ion-exchange chromatography on Superose SP FF. Purified products from both methods were analyzed for their antagonistic activity against *Camplylobacter jejuni*. SDS-PAGE and isoelectrofocusing (IEF) were performed. Results are summarized below in Tables 3 and 4.

Specific activity of the preparations purified by method B was found to be 4-fold higher than activity of the same product obtained by method A. It took approximately 12.5 hours to produce the preparation by method B versus 52 hours using method A. Method B reduces the number of steps required for purification of bactericin from CAP by eliminating gel filtration and hydrophobic interaction chromatography and only applying ion-exchange chromatography.

The amino acid sequences of purified bacteriocins were determined by Edman degradation using a 491 cLC automatic sequencer (Applied Biosystems, USA). The bacteriocins were hydrolyzed in about 6M HCl under a vacuum at approximately 110° C. for about 72 hours. Molecular weights of bacteriocins 50-52 and 760 were determined by mass spectrometry using a Voyager-DERP (Perkin-Elmer, USA). The MALDI-TOF system, a matrix-assisted laser desorption ionization time of flight system, was used along with matrix, 2-cyano-hydroxycinnamic acid. The amino acid sequences are:
50-52:TTKNYGNGVCNSVNWCQCGNVWASCN-LATGCAAWLCKLA SEQ ID NO 1
760:NRWYCNSAAGGVGGAAVCGLAGYVGEAK-ENIAGEVRKGWGMAGGFTHN KACKSFPGSG-WASG SEQ ID 2
Calculated molecular weights of the peptides were about 3.9 kDa for bacteriocin 50-52 and about 5.5 kDa for bacteriocin 760. Analysis by MALDI-TOF revealed the following molecular weights: about 3,932 Da for bacteriocin 50-52 and about 5,362 Da for bacteriocin 760.

EXAMPLE 6

The influence of enzymes, temperature, and pH on bacteriocin activity was determined. About 10 ml of one of the following enzymes were transferred into tubes containing about 20 ml of bacteriocins: beta-chymotrypsin-about 100 mg/ml, proteinase K-about 200 mg/ml, papain-about 60 mg/ml, lysozyme-about 750 mg/ml, and lipase-about 100 mg/ml (all from Sigma-Aldrich Corp., St. Louis Mo.). After about a three hour incubation period at about 37° C., the mixture of bacteriocin and enzyme was analyzed for antimicrobial activity using the spot test as in Example 3. Untreated bacteriocins served as positive controls.

To study the thermostability of bacteriocins, about a 2 mg/ml sample was boiled in a water bath for about 15 minutes, cooled, and assessed in terms of their antimicrobial activity. Approximately 2 mg/ml of bacteriocin was used to evaluate the effect of pH. About 2 milliliters of sterile solutions, about 10 mM NaOH or about 10 mM HCl were added

TABLE 3

Comparative data on specific activity of bacteriocins 760 and 50-52 isolated using Methods A and B.

| Methods of isolation | Bacteriocin 760 | | | | | Bacteriocin 50-52 | | | | |
|---|---|---|---|---|---|---|---|---|---|---|
| | Amount of protein mg | Activity UE/ml | Specific Activity UE/ml | SDS Page | IEF | Amount of protein mg | Activity UE/ml | Specific Activity UE/ml | SDS Page | IEF |
| Method A | 0.08 | 12,800 | 71,111 | 5.5 kD | 9.5 | 0.075 | 6,400 | 85,333 | 3.9 kD | 8.4 |
| Method B | 0.18 | 51,200 | 284,444 | 5.5 KD | 9.5 | 0.04 | 12,800 | 320,000 | 3.9 KD | 8.4 |

TABLE 4

Antimicrobial activity of purified bacteriocins 760 and 50-52 determined by Spot Test, SDS-Page, and Isoelectrofocusing (IEF).

| Bacteriocin | Test Strain | Inhibiting Activity, Spot Test (AU/ml) | Inhibiting Activity SDS-PAGE (kDa) | Inhibiting Activity IEF |
|---|---|---|---|---|
| 760 | *C. jejuni* | 51,200 | +Band 1 m.w. = 5.5 | +Band 1 pI = 9.5 |
| | *S. enteritidis* 204 | 12,800 | +Band 1 m.w. = 5.5 | +Band 1 pI = 9.5 |
| | *E. coli* O157:H7 | 12,800 | +Band 1 m.w. = 5.5 | +Band 1 pI = 9.5 |
| 50-52 | *C. jejuni* | 12,800 | +Band 1 m.w. = 3.9 | +Band 1 pI = 8.4 |
| | *S. enteritidis* 204 | 12,800 | +Band 1 m.w. = 3.9 | +Band 1 pI = 8.4 |
| | *E. coli* O157:H7 | 6,400 | +Band 1 m.w. = 3.9 | +Band 1 pI = 8.4 | to samples to test pH from about 3 to about 10. Samples were incubated at about 37° C. for about 2 hours and 24 hours, and at about 90° C. for about 20 minutes. Samples were adjusted to a pH of about 7.2 by addition of about 4 mM sterile phosphate buffer and analyzed for their antimicrobial activity using the spot test as described above in Example 3.

The bacteriocins 50-52 and 760 lost their antimicrobial activity after being treated with beta-chymotrypsin, proteinase K, and papain, but retained it when treated with lysozyme, lipase, or heating to about 90° C. (Table 5). They were stable at different values of pH ranging from about 3.0 to about 9.0, but became inactive at about pH 10 (Tables 5 and 6).

TABLE 5

Effect of enzymes and temperature on antimicrobial activity of bacteriocins

| Treatment | Activity* |
|---|---|
| beta-chymotrypsin | − |
| proteinase K | − |
| Papain | − |
| lysozyme | + |
| lipase | + |
| 100° C., 15 minutes | + |

*activity determined by spot test, with *C. jejuni* NCTC 11168 as indicating strain.
+ presence of activity
− absence of activity after treatment with enzymes or exposure to temperature

TABLE 6

Effect of pH on activity of bacteriocins.

| | Activity determined by spot test with *C. jejuni* NCTC 11168 | | |
|---|---|---|---|
| pH | 20 min @ 90° C. | 2 h @ 37° C. | 24 h @ 37° C. |
| 3.0 | + | + | + |
| 5.0 | + | + | + |
| 6.2 | + | + | + |
| 7.0 | + | + | + |
| 8.4 | + | + | + |
| 9.1 | + | + | + |
| 10.0 | − | − | − |

+ presence of activity
− absence of activity

EXAMPLE 7

The susceptibility of *Campylobacter* spp. to purified preparations of bacteriocins 760 and E50-52 was determined using strains isolated from broiler chicks as described above in Example 1. Antagonistic activity of the bacteriocins was assessed on the basis of minimum inhibitory concentrations (MICs) which were determined by agar diffusion. Table 7 below shows the Bacteriocin MICs for the strains tested. All the tested bacteriocins are highly antagonistic to the *Campylobacter* spp. strains. Strain 760 is much more active than the remaining ones with MICs of between about 0.05 to about 0.1 µg/ml.

TABLE 7

Bacteriocin MICs for strains of *Campylobacter* spp.

| | MICs (ug/ml) | | | | |
|---|---|---|---|---|---|
| Strains | OR7 | B1580 | B37 | 760 | E50-52 |
| P-24 | 1.6 | 0.8 | 0.8 | 0.05 | 0.05 |
| P-32 | 0.08 | 0.08 | 1.6 | 0.05 | 0.1 |
| P-27 | 0.8 | 0.8 | 0.8 | 0.05 | 0.1 |
| I/U-1 | 1.6 | 0.4 | 1.6 | 0.05 | 0.05 |
| P-31 | 3.2 | 1.6 | 0.8 | 0.05 | 0.1 |
| P-28 | 0.4 | 3.2 | 0.8 | 0.05 | 0.1 |
| G-2 | 0.8 | 1.6 | 0.8 | 0.05 | 0.1 |
| G-1 | 0.8 | 1.6 | 0.8 | 0.05 | 0.05 |
| Ind18/2 | 0.4 | 1.6 | 3.2 | 0.05 | 0.05 |
| Cez-4 | 0.2 | 0.2 | 0.2 | 0.1 | 0.1 |
| P-21 | 0.8 | 0.4 | 0.4 | 0.1 | 0.05 |
| K-10 | 0.4 | 0.4 | 1.6 | 0.05 | 0.05 |
| F-1 | 0.2 | 0.8 | 3.2 | 0.05 | 0.1 |
| B-3 | 0.1 | 1.6 | 0.2 | 0.05 | 0.05 |
| P-2 | 0.1 | 0.4 | 0.4 | 0.05 | 0.05 |

EXAMPLE 8

The susceptability of Gram-positive and Gram-negative bacteria to bacteriocins 760 and 50-52 was determined using a spot-test as described above in Example 3. Results are presented in Tables 8 and 9. As seen from Table 8, bacteriocin 760 has a wide spectrum and high level of antagonistic activity. The bacteriocin inhibits the growth of both Gram-positive and Gram-negative bacteria. Its MIC for test strains ranges from about 0.1 µg/ml to about 3.2 µg/ml. As seen in Table 9, bacteriocin 50-52 has a wide spectrum and high level of antagonistic activity. The bacteriocin inhibits the growth of both Gram-positive and Gram-negative bacteria. Its MIC for test strains ranges from about 0.1 µg/ml to about 3.2 µg/ml.

TABLE 8

Antibacterial Activity of bactericin 760 determined by Spot Test.

| Test Strains | MIC, mg/ml |
|---|---|
| *S. enteritidis* 1 | 0.2 |
| *S. enteritidis* 4 | 0.4 |
| *S. enteritidis* 204 | 0.2 |
| *S. enteritidis* 237 | 0.2 |
| *S. choleraesuis* 434/4 | 0.4 |
| *S. choleraesuis* 370 | 0.4 |
| *S. typhimurium* 383/60 | 0.4 |
| *S. typhimurium* 320 | 0.2 |
| *S. gallinarum pullorum* | 0.4 |
| *E. coli* HB101 | 0.1 |
| *E. coli* C600 | 0.1 |
| *E. coli* O157:H7 Y-63 | 1.6 |
| *E. coli* O157:H7 G-3 | 1.6 |
| *E. coli* O157:H7 OD-3 | 1.6 |
| *E. coli* O157:H7 lab. 39 | 1.6 |
| *Y. enterocolitica* 03 | 0.1 |
| *Y. enterolitica* 09 | 0.1 |
| *Y. enterolitica* 04 | 0.1 |
| *Citrobacter freundi* | 1.6 |
| *Klebsiella pneumoniae* | 3.2 |
| *Sh. dysenteriae* | 0.1 |
| *Staphylococcus aureus* | 1.6 |
| *Staphylococcus epidermidis* | 1.6 |
| *Y. pseudotuberculosis* | 3.2 |
| *Y. pseudotuberculosis* | 3.2 |
| *Pseudomonas aeruginosa* 25583 | 0.4 |
| *Proteus mirabilis* | 3.2 |
| *Morganella morganii* | 3.2 |
| *L. monocytogenes* 9-72 | 0.1 |
| *C. jejuni* L4 | 0.1 |

TABLE 9

Antibacterial Activity of bacteriocin 50-52 determined by Spot Test.

| Strains | MICs (μg/ml) |
|---|---|
| S. enteritidis 1 | 0.1 |
| S. enteritidis 4 | 0.1 |
| S. enteritidis 204 | 0.2 |
| S. enteritidis 237 | 0.1 |
| S. choleraesuis 434/4 | 0.1 |
| S. choleraesuis 370 | 0.1 |
| S. typhimurium 383/60 | 0.1 |
| S. typhimurium 320 | 0.1 |
| S. gallinarum pullorum | 0.1 |
| E. coli HB101 | 0.1 |
| E. coli C600 | 0.1 |
| E. coli O157:H7 Y-63 | 0.1 |
| E. coli O157:H7 G-3 | 0.1 |
| E. coli O157:H7 OD-3 | 0.1 |
| E. coli O157:H7 lab. 39 | 0.1 |
| Y. enterolitica 03 | 0.1 |
| Y. enterolitica 09 | 0.4 |
| Y. enterolitica 04 | 0.1 |
| Citrobacter freundi | 0.1 |
| Klebsiella pneumoniae | 0.2 |
| Sh. dysenteriae | 0.4 |
| Staphylococcus aureus | 0.4 |
| Staphylococcus epidermis | 3.2 |
| Y. pseudotuberculosis | 0.4 |
| Pseudomonas aeruginosa 25583 | 3.2 |
| Proteus mirabilis | 1.6 |
| Morganella morganii | 3.2 |
| L. monocytogenes 9-72 | 0.2 |
| C. jejuni L-4 | 0.2 |

EXAMPLE 9

The minimal inhibiting concentrations (MICs) of bacteriocins 760 and 50-52 and Methicillin were determined by Spot Test. Various concentrations of purified bacteriocins (μg/ml) in a volume of 10 μl was added to cultures of *Staphylococcus aureus, Staphylococcus epidermidis, Pseudomonas aeruginosa,* and *Helicobacter pylori*. The cultures were incubated for about 24 hours at about 37° C. under aerobic conditions for all but *Helicobacter pylori* which was incubated under microaerobic conditions. Results are shown below in Table 10.

TABLE 10

MIC of bacteriocins for *Staphylococcus aureus, Staphylococcus epidermidis, Pseudomonas aeruginosa,* and *Helicobacter pylori*.

| Bacteriocin or antibiotic | MIC of purified Bacteriocins and Antibiotic (μg/ml) | | | |
|---|---|---|---|---|
| | S. aureus | S. epidermidis | P. aeruginosa | H. pylori |
| 760 | 1.6 | 1.6 | 0.4 | 0.2 |
| 50-52 | 0.1 | 0.4 | 0.8 | 0.8 |
| Methicillin | 52.5 | 64.8 | 78.4 | 93.8 |

The foregoing detailed description is for the purpose of illustration. Such detail is solely for that purpose and those skilled in the art can make variations without departing from the spirit and scope of the invention.

What is claimed is:

1. An isolated bacteriocin produced by NRRL B-30745.

2. The bacteriocin of claim 1 having an amino acid sequence of SEQ ID NO :2.

3. Isolated strain NRRL B-30745.

4. A therapeutic composition comprising:
   a. at least one isolated bacteriocin produced by deposited strain NRRL B-30745, in an amount effective to at least reduce levels of colonization by at least one target bacteria; and
   b. a suitable therapeutic carrier.

5. The therapeutic composition of claim 4 wherein said bacteriocin has an amino acid sequence SEQ ID NO: 2.

6. A therapeutic feed for animals comprising:
   a. at least one isolated bacteriocin produced by deposited strain NRRL B-30745, in an amount effective to at least reduce levels of colonization by at least one target bacteria,
   b. a suitable therapeutic carrier, and
   c. an animal feed.

7. The therapeutic feed of claim 6 wherein said at least one bacteriocin has an amino acid sequence of SEQ ID NO: 2.

* * * * *